US006699972B1

(12) United States Patent
Roffler et al.

(10) Patent No.: US 6,699,972 B1
(45) Date of Patent: Mar. 2, 2004

(54) CHIMERIC PROTEIN AND METHOD OF CONTROLLING TUMOR GROWTH USING THE PROTEIN

(75) Inventors: Steve R. Roffler, Taipei (TW); Kuang-Wen Liao, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/602,263

(22) Filed: Jun. 23, 2000

Related U.S. Application Data

(60) Provisional application No. 60/141,151, filed on Jun. 25, 1999.

(51) Int. Cl.$^7$ .......................... A61K 38/00; C07K 14/00; C12P 21/08; C12N 5/06; C12N 5/02
(52) U.S. Cl. ..................... 530/387.3; 530/300; 530/350; 435/325; 435/326; 424/93.1; 424/93.2; 424/93.21
(58) Field of Search ................................. 530/300, 350, 530/387.3; 435/325, 326; 424/93.1, 93.2, 93.21

(56) References Cited

U.S. PATENT DOCUMENTS 5,712,149 A * 1/1998 Roberts .................... 435/252.3

OTHER PUBLICATIONS

Chou et al., "Expression of Chimeric Monomer and Dimer Proteins on the Plasma Membrane of Mammalian Cells", pp. 160–169, Biotechnology and Bioengineering, vol 65, No. 2, Oct. 20, 1999.
Liao et al., "Activation of lymphocytes by anti–CD3 single–chain antibody dimers expressed on the plasma membrane of tumor cells", pp. 339–347, Gene Therapy (2000) 7.
Kulkarni et al., "Programmed Cell Death Signaling Via Cell–Surface Expression of a Single–Chain Antibody Transgene", pp. 1209–1217, Transplantation, vol. 69, No. 6, Mar. 27, 2000.
Kontermann et al., "Intracellular and cell surface displayed single–chain diabodies", pp. 179–188, Journal of Immmunological Methods 226 (1999).
Rode et al., "T cell activation by monoclonal antibodies bound to tumor cells by a cell surface displayed single–chain antibody", pp. 151–160, Journal of Immunological Methods 224 (1999).
Chesnut et al., "Selective isolation of transiently transfected cells from a mammalian cell population with vectors expressing a membrane anchored single–chain antibody", pp. 17–27, Journal of Immunological Methods 193 (1999).
Ines et al., "Apoptosis of a Human Melanoma Cell Line Specifically Induced by Membrane–Bound Single–Chain Antibodies", pp. 3948–3956, Journal of Immunological Methods 163 (1999).

Yang et al., "Antitumor Immunity Elicited by Tumor Cells Transfected with B7–2, a Second Ligand for CD28/CTLA–4 Costimulatory Molecules", pp. 2794–2800, Journal of Immunological Methods 154 (1995).
Griffin et al. "Blockade of T Cell Activation Using a Surface–Linked Single–Chain Antibody to CTLA–4 (CD152)", pp. 4433–4442, Journal of Immunological Methods 164 (2000).
Alvarez–Vallina et al., "Antigen–Specific targeting of CD28–mediated T cell co–stimulation using chimeric single–chain antibody variable fragment–CD28 receptors", pp. 2304–2309, Eur. J. Immunol. 26 (1996).
Brocker et al., "New simplified molecular design for functional T cell receptor", pp. 1435–1439, Eur. U. Immunol. 23 (1993).
"Cell Surface Display of a Single–Chain Antibody for Attaching Polypeptides", pp. 650–658, BioTechniques vol. 21, No. 4 (1996).
Freeman et al., "Murine B7–2, an alternative CTLA4 Counter–receptor that Costimulates T Cell Proliferation and Interleukin 2 Production", pp. 2185–2192, The Journal of Experimental Medicine, vol. 178, Dec. 1993.
Tibben et al., "Pharmacokinetics, Biodistribution and Biological Effects of Intravenously Administered Bispecific Monoclonal Antibody OC/TR F9(ab')$_2$ In Ovarian Carcinoma Patients", pp. 477–483, Int. J. Cancer: 66, (1996).
Chen et al., "Tumor Immunogenicity Determines the Effect of B7 Costimulation on T Cell–mediated Tumor Immunity", pp. 523–532, J. Exp. Med. © The Rockefeller University Press. vol. 179 Feb. (1994).
Moritz et al., "Cytotoxic T lymphocytes with a grafted recognition specificity for ERBB2–expressing tumor cells", pp. 4318–4322, Proc. Natl. Acad. Sci. USA vol. 91, May 1994.
Krause et al., "Antigen–dependent CD28 Signaling Selectively Enhances Survival and Proliferation in Genetically Modified Activated Human Primary T Lymphocytes", pp. 619–626, J. Exp. Med © The Rockefeller University Press. vol. 188, No. 4, Aug. 17, 1998.
Altenschmidt et al., "Specific cytotoxic T lymphocytes in gene therapy", pp. 259–266, J. Mol. Med. 75 (1997).
Altenschmidt et al., "Adoptive Transfer of In Vitro–Targeted, Activated T Lymphocytes Results in Total Tumor Regression", pp. 5509–5515, The Journal of Immunology, 159, (1997).

* cited by examiner

*Primary Examiner*—Anne M. Wehbe'
(74) *Attorney, Agent, or Firm*—Cohen, Pontani, Lieberman & Pavane

(57) ABSTRACT

A chimeric protein expressed from a transgene tranduced into a mammalian tumor cell and method of using the chimeric protein for cancer treatment. The chimeric protein comprises an effector and an anchor, which are linked by a spacer. The chimeric protein, when expressed and exposed on the tumor cell surface in vivo can activate T cells, which further lead to lysis of the tumor cells. The anti-tumor effects can be enhanced by co-expression of certain co-stimulators, such as CD80 or CD86.

4 Claims, 15 Drawing Sheets

SEQUENCE LISTING

```
<160> NUMBER OF SEQ ID NOS: 6

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 1
tgctggggcc cagccggccg acatccagat gacccagtct ccatc              45

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 2
accgccgccc gaagtactgc cccgtttgat ttccagcttg gtgccagg           48

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 3
aagtcgagtg agggtaaggg tgaggtgcag ctggtggagt ctggggga          48

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 4
tgttgtgtcg actgaggaga cggtgaccat ggttccttg                     39

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Primer
```

```
<400> SEQUENCE: 5
ggcagtactt cgggcgccgg taagtcgagt gagggtaagg gt                              42

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Thr Ser Gly Ala Gly Lys Ser Ser Glu Gly Lys Gly
 1               5                  10
```

CHIMERIC PROTEIN AND METHOD OF CONTROLLING TUMOR GROWTH USING THE PROTEIN

RELATED APPLICATIONS

This application claims priority from U.S. Provisional Patent Application Serial No. 60/141,151, filed Jun. 25, 1999.

BACKGROUND OF THE INVENTION

1. Field of the Invention

The present invention relates to a chimeric protein expressed from a transgene tranduced into tumor cells. Particularly, the invention pertains to a chimeric protein which, when expressed on tumor cells, can promote T cell activation without relying on the concurrent presence of either tumor-associated antigens or MHC molecules. Such T cell activation can lead to lysis of the tumor cells as well as bystander killing of non-transduced tumor cells in the vicinity and are therefore of great significance in cancer treatment.

2. Description of the Related Art

It is known in the art that cytotoxic T cells can recognize and kill tumor cells that express peptides derived from tumor associated antigens on their surface in association with MHC class I molecules. The identification of a wide range of tumor associated antigens from melanoma and other tumor cells has generated interest in developing strategies that employ activated CD8$^+$ T cells for selective killing of tumor cells. Many tumors, however, display defects; in antigen processing and presentation. Stable expression of MHC class I molecules on the cell surface requires proteolytic generation of peptides by the proteosome in the cytosol and subsequent delivery of cytosolic peptides to the endoplasmic reticulum by the peptide transporters TAP1 and TAP2 (Goldberg and Rock 1992). Loss or downregulation of proteosome subunits, TAP-1, TAP-2, β2-microglobulin or MHC class I heavy chain have been documented for a wide range of solid tumors including melanoma (Maeurer et al. 1996) and prostate (Blades et al. 1995), lung (Korkolopoulou et al. 1996), bladder (Nouri et al. 1994), renal (Luboldt et al. 1996), colorectal (Kaklamanis et al. 1994), and breast (Vitale et al. 1998) carcinomas. Defective presentation of peptides by MHC class I molecules can allow tumor escape from immune recognition by CD8$^+$ T cells (Restifo et al. 1996).

It is also known in the art that to overcome defects in antigen processing and presentation in tumor cells, cytotoxic T cells can be targeted to lyse tumor cells in a way that does not rely on the presence of MHC molecules on the tumor cells. One such method is through the use of chimeric antigen receptors expressed on T-cells. Such chimeric receptors have a single-chain antibody (scFv) fused to the zeta chain of the TCR CD3 complex and can be expressed on T-cells (Moritz et al. 1994; Altenschmidt et al. 1997; Altenschmidt et al. 1997; Alvarez Vallina et al. 1997). Another method is by intravenous administration of bispecific antibodies. Bispecific antibodies, that is, antibodies with specificity for both the CD3 molecule of T cells and surface antigens of tumor cells, can redirect activated T cells to attack and lyse tumor cells (Bolhuis et al. 1991). However, application of either method relies on the identification of tumor associated antigens that are preferentially expressed on the surface of tumor cells. Moreover, intravenous administration of bispecific antibodies can induce systemic cytokine release and toxicity (Weiner et al. 1995; Tibben et al. 1996).

The present invention discloses an alternative approach to promote T cell activation and lysis of tumor cells that is independent of the expression of antigens or MHC molecules on the tumor cells. This method, unlike the prior art methods, does not rely on the identification of any tumor associated antigens and does not induce systemic cytokine release and toxicity.

SUMMARY OF THE INVENTION

In accordance of the present invention, activation of T cells as a means of destroying tumor cells can be achieved by one or more chimeric surface proteins expressed from transgenes transduced into in vivo tumor cells or into ex vivo tumor cells which are then injected back in the tumor. Expression of the chimeric proteins on tumor cells can led to T cell activation, further resulting in lysis of the tumor cells. Thus, the chimeric proteins can be employed to destroy tumor cells in vivo, forming the basis of a new method for treating cancers.

As a preferred embodiment of the present invention, a chimeric protein, 2C11-γ1-B7, has shown a significant T-cell activating property when expressed on mammalian cells in vivo. Further, when co-expressed with costimulatory molecules such as CD80 or CD86, the potency of 2C11-γ1-B7 activation of T cells increases by several hundred folds. Also of significance is the inclusion of a spacer γ1 (the hinge-CH2—CH3 region of human IgG$_1$) between the effector (here, 2C11 single chain antibody) and anchor (B7, composed of the transmembrane domain and cytoplasmic tail of murine B7-1). The effector has the ability to activate T cells while the anchor is responsible for attaching the effector to the cell membrane. The spacer, on the other hand, can prevent or reduce proteolytic cleavage of the effector from the anchor. The method of activating T cells of the present invention is not limited to the particular chimeric proteins employed in the preferred embodiment, other proteins may be satisfactorily used as long as they can be expressed on the tumor cell surface.

Another objective of the invention is to more efficiently express chimeric proteins on the surface of mammalian cells in vivo. One major limitation on high level expression of chimeric surface proteins is proteolytic cleavage, which may in some cases reduce the expression to an undetectable level. This objective is achieved by introducing a spacer between the effector (i.e., the functional domain for T cell activation) and the anchoring transmembrane (TM) domain. Such arrangement dramatically reduces the proteolytic cleavage that usually occurs between the functional domain, such as scFv (2C11) and the TM. Of course, the invention is not limited to γ1, which is used as an example in the preferred embodiment, other spacers may be satisfactorily used.

Still another objective of the invention is developing a method for treating cancers in mammals. This objective is achieved by using one of known gene transduction methods, such as direct injection of the transgenes into the tumors under treatment or through a viral delivery method (adenovirus or retrovius), to introduce transgenes into the tumor cells whereby the chimeric surface proteins with capability of activating T cells can be expressed. The specific transgene delivery method is not a limitation to the present invention. Any efficient existing or future developed technologies may be employed. For example, the following references disclose several transgene delivery methods employed in various situations:

Nagamachi Y, et al., "Suicidal gene therapy for pleural metastasis of lung cancer by liposome-mediated transfer of herpes simplex virus thymidine kinase gene", *Cancer Gene Ther.* 6:546–53 (1999), where a transgene-encoding plasmid was mixed with liposomes to form a DNA-liposome complex. The mixture was injected interpleurally to mice that had lung cancer cells growing in the pleural cavity. The transgene was expressed in about 14% of the tumor cells in the pleural cavity.

Cao G, et al., "Analysis of the human carcinoembryonic antigen promoter core region in colorectal carcinoma-selective cytosine deaminase gene therapy", *Cancer Gene Ther.* 6:572–80 (1999), where a retrovirus vector was constructed such that the gene of interest is expressed under the control of the CEA promoter. Nude mice that had established i.p. human colorectal carcinoma tumors were i.p. injected with retrovirus-producing cells, and the transgene was expressed in the tumors.

Puhlmann M, et al., "Vaccinia as a vector for tumor-directed gene therapy: biodistribution of a thymidine kinase-deleted mutant", *Cancer Gene Ther.* 7:66–73 (2000), where an attunuated replication-competent vaccinia virus was used as a vector for in vivo tumor transduction. The vaccinia virus was administered interperitoneally to mice that had established i.p. tumors. The reporter gene expression in i.p. tumors was up to 7000 times higher than in normal tissues. Intraveneous administration of the vaccinia virus resulted in much higher transgene expression (up to 180,000 fold difference) in sub cutaneous tumors compared to normal tissues.

Gambotto A, et al. "Induction of antitumor immunity by direct intratumoral injection of a recombinant adenovirus vector expressing interleukin-12", *Cancer Gene Ther.* 6:45–53 (1999), where an adenoviral vector was constructed to express a gene under the control of the early cytomegalovirus immediate-early promoter, and the recombinant adenovirus were directly injected into murine tumors.

Gunji Y, et al. "Inhibition of peritoneal dissemination of murine colon carcinoma cells by administrating retrovirus harboring IL-2 gene", *Cancer Gene Ther.* 5:339–43 (1998), where a retrovirus was injected into mouse i.p. tumors in vivo in which it expressed the gene of interest and showed therapeutic benefits.

Shirakawa T, et al., "In vivo suppression of osteosarcoma pulmonary metastasis with intravenous osteocalcin promoter-based toxic gene therapy", *Cancer Gene Ther.* 5:274–80 (1998), where a recombinant adenoviral vector was constructed such that the gene of interest is expressed under the control of an osteocalcin promoter, and was then i.v. injected into nude mice that had established osteosarcoma metastasis in their lungs, resulting a specific expression of a reporter gene in the lung tumors of such mice.

Kwong Y L, et al., "Adenoviral-mediated suicide gene therapy for hepatic metastases of breast cancer", *Cancer Gene Ther.* 3:339–44 (1996), where breast cancer tumors were established in the livers of mice. The gene of interest was cloned into a replication defective adenoviral vector. The vector was directly injected into tumors where it allowed expression of the transgene.

Ichikawa T, et al., "In vivo efficacy and toxicity of 5-fluorocytosine/cytosine deaminase gene therapy for malignant gliomas mediated by adenovirus. *Cancer Gene Ther.* 7:74–82 (2000), where a transgene of interest was placed in a vector and used to make adenovirus that carried the gene. The resulting adenovirus was directly injected into a brain tumor in rats where the tumor cells were infected with the virus, thereby expressing the gene.

Of course, there are possibly other suitable transgene delivery methods, either existing now or to be developed in the future. The specific transgene delivery method used, however, forms no part of the invention of cancer treatment.

Other objects and features of the present invention will become apparent from the following detailed description considered in conjunction with the accompanying drawings. It is to be understood, however, that the description and drawings are provided solely for purposes of illustration and not as a definition of the limits of the invention, for which reference should be made to the claims.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, like reference characters denote similar elements throughout the several views.

ABBREVIATIONS

γ1, the hinge-$CH_2$—$CH_3$ region of human IgG,
2C11, anti-CD3 epsilon chain scFv
2C11-B7, 2C11 scFv fused to the transmembrane domain and cytoslic tail of murine B7-1.
2C11-γ1-B7, 2C11-B7 with the γ1 domain fused between the 2C11 scFv and B7 domains
2C11-PDGFR, 2C11 scFv fused to the transmembrane domain and truncated cytosolic tail of the PDGFR
2C11-γ1-PDGFR, 2C11-PDGFR with the γ1 domain fused between the 2C11 scFv and PDGFR domains
BALB/2C11, BALB/3T3 cells that express 2C11-γ1-B7
BALB/2C11/CD80, BALB/3T3 cells that express 2C11-γ1-B7 and B7-1
BALB/2C11/CD86, BALB/3T3 cells that express 2C11-γ1-B7 and B7-2
BALB/phOx, BALB/3T3 cells that express phOx-γ1-B7
BALB/phOx/CD80, BALB/3T3 cells that express phOx-γ1-B7 and B7-1

BALB/phOx/CD86, BALB/3T3 cells that express phOx-γ1-B7 and B7-2

B7, the transmembrane and cytosolic domains of murine B7-1, employed for surface expression.

CD80, costimulation molecule also known as B7-1

CD86, costimulation molecules also known as B7-2

CT26/2C11, CT26 colon cancer cells expressing 2C11-γ1-B7

CT26/neo, CT26 colon cancer cells transfected with control vector pcDNA3

F1/2C11, B16/F1 cells expressing that express 2C11-γ1-B7

F1/2C11/CD80, B16/F1 cells expressing that express 2C11-γ1-B7 and B7-1

F1/2C11/CD86, B16/F1 cells expressing that express 2C11-γ1-B7 and B7-2

F1/phOx, B16/F1 cells that express phOx-γ1-B7

F1/phOx/CD80, B16/F1 cells that express phOx-γ1-B7 and B7-1

F1/phOx/CD86, B16/F1 cells that express phOx-γ1-B7 and B7-2

PDGFR, platelet-derived growth factor receptor phOx, anti-4-ethoxymethylene-2-phenyl-2-oxazolin-5-one scFv phOx-B7, phOx scFv fused to the transmembrane domain and cytoslic tail of murine B7-1 phOx-γ1-B7, phOx-B7 with the γ1 domain fused between the 2C11 scFv and B7 domains TCR, T-cell receptor TM, transmembrane domain scFv, single-chain antibody fragment

DETAILED DESCRIPTION OF THE PRESENTLY PREFERRED EMBODIMENTS

The following described embodiment demonstrates that a chimeric protein, 2C11scFv, can be expressed on the surface of tumor cells and that such expression enhances T cell activation which leads to lysis of the tumor cells.

Surface Expression of scFv-TM Chimeric Proteins

Figure 1:
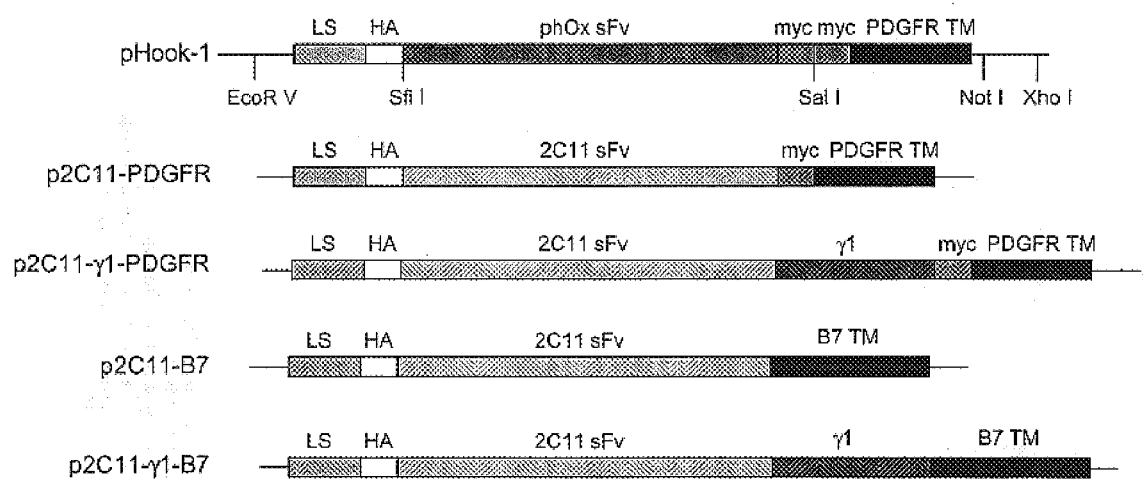
FIG. 1 depicts the genetic construction of the transgenes encoding the membrane-bound chimeric proteins used in one embodiment of the present invention.

The cDNA encoding the 2C11 single-chain antibody (2C11scFv) was generated by RT-PCR from 145.2C11 hybridoma cells. mAb 145.2C11 is an antibody, which binds to the epsilon chain of the CD3 complex on murine T cells. With reference to FIG. 1, p2C11-γ1-PDGFR was constructed by replacing the single-chain antibody cDNA in pHook-1 with the gene encoding 2C11scFv and inserting the γ1 domain sequence (hinge-$CH_2$—$CH_3$ region) of human IgG, between the scFv and TM cDNA. This plasmid encodes a chimeric protein composed of the murine immunoglobulin κ chain signal peptide, an HA epitope, the anti-CD3 scFv gene, the γ1 domain, a myc epitope and the transmembrane domain (TM) of the PDGFR (platelet-derived growth factor receptor). p2C11-γ1-B7 encodes a similar chimeric protein except for the substitution of the TM and cytoplasmic tail of murine B7-1 for the PDGFR TM. The PDGFR and B7-1 TM are designed to anchor the 2C11 scFv to the cell surface whereas the γ1 domain should allow the formation of disulfide-linked dimers.

Figure 2:
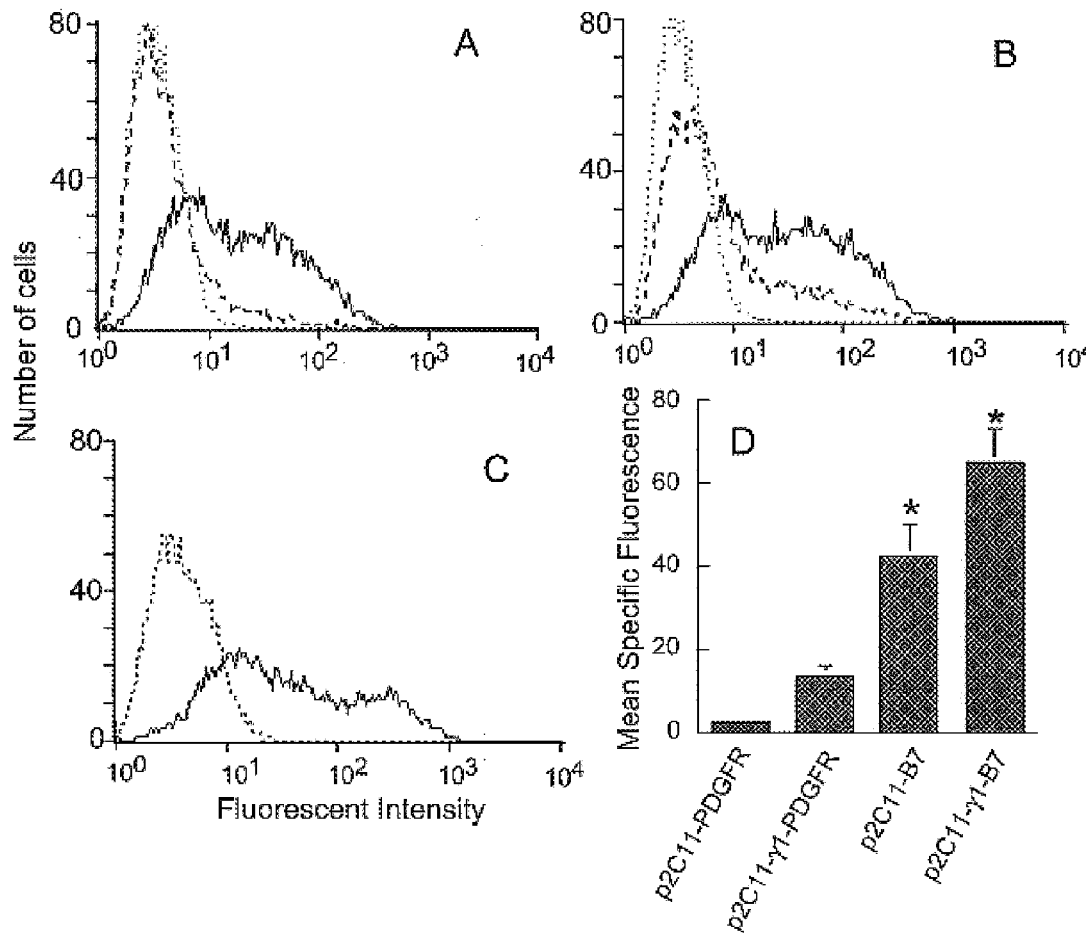
FIG. 2(A–D) is the surface immunofluorescence data showing the expression of 2C11 scFv in comparison with other chimeric proteins.

The ability of chimeric 2C11scFv proteins to be expressed on the surface of cells was examined by flow cytometer analysis. In FIG. 2A, BHK cells were transfected with pcDNA3 (dotted line), p2C11-PDGFR (dashed line) or p2C11-B7 (solid line). In FIG. 2B, BHK cells were transfected with pcDNA3 (dotted line), p2C11-γ1-PDGFR (dashed line) or p2C11-γ1-B7 (solid line). In FIG. 2C, BALB/3T3 cells were transfected with pcDNA3 (dotted line) or p2C11-γ1-B7 (solid line). After 48 h, cells were stained with mAb 12CA5 against the HA epitope followed by FITC-conjugated goat anti-mouse IgG $(Fab')_2$ before the immunofluorescence of $10^4$ viable cells was measured with a FACS caliber flow cytometer. FIG. 2A shows that transfection of BHK cells with p2C11-PDGFR resulted in only minimal expression of scFv on the cell surface whereas high levels of 2C11-B7 were detected after transfection with p2C11-B7. Similarly, much higher levels of 2C11-γ1-B7 were detected on the surface of BHK cells compared to 2C11-γ1-PDGFR (FIG. 2B). High levels of 2C11-γ1-B7 were also expressed on transfected BALB/3T3 cells (FIG. 2C). In FIG. 2D, quantitation of scFv surface expression in three independent experiments revealed that the mean fluorescence of BHK cells expressing 2C11-B7 or 2C11-γ1-B7 chimeric proteins was significantly greater than chimeric proteins employing the PDGFR TM. Significant differences between chimeric proteins containing the B7-1 and PDGFR TM domains are indicated: *, $p \leq 0.05$. Bars represent the standard error of the mean.

Chimeric scFv Forms Dimers

Figure 3:
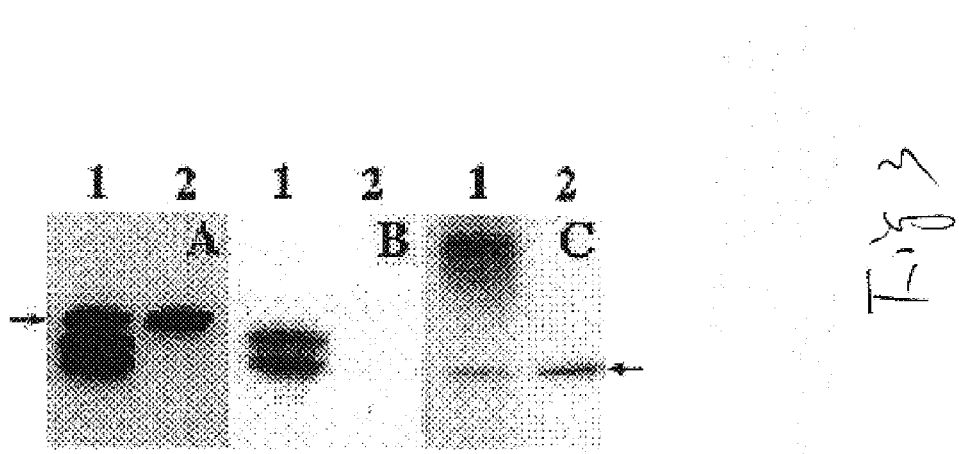
FIG. 3(A–C) is the immunoblot data showing dimer formation of 2C11 scFv.

The expression of 2C11-γ1-B7 chimeric protein was examined by immunoblotting whole cell lysates prepared from BHK cells that were transfected with p2C11-γ1-B7. $5 \times 10^4$ BHK cells that were transfected with p2C11-γ1-B7 (lane 1) or pcDNA3 (lane 2) were lysed and separated on a 8% reduced (A and B) or non-reduced (C) SDS-PAGE. Proteins transferred to nitrocellulose paper were immunoblotted with mAb 12CA5 against the HA epitope (A and C) or HRP-conjugated goat anti-human IgG Fc-specific antibody (B). The position of the cross-reactive protein bound by mAb 12CA5 is indicated by an arrow in A and C. Immunoblotting with anti-HA mAb against the N-terminal epitope of the chimeric protein showed that BHK cells transfected with either pcDNA3 or p2C11-γ1-B7 displayed a common non-specific band. Only BHK cells transfected with p2C11-γ1-B7, however, displayed a specific band corresponding to the predicted molecular weight of 2C11-γ1-B7 monomer (FIG. 3A, lane 1). An additional band that migrated more rapidly is likely due to cleavage of the 2C11-γ1-B7 chimeric protein between the γ1 and B7 TM domains based on the estimated size of the protein. Both the 2C11-γ1-B7 chimeric protein and degradation product contained the γ1 domain as shown by binding of goat anti-human IgG Fc-specific antibody (FIG. 3B, lane 1), further localizing the cleavage site to between the γ1 domain and B7 TM. The doublet is unlikely due to differences in glycosylation because tunicamycin treatment increased the migration of both bands (results not shown). Electrophoreses of the transfected cells on a non-reducing SDS-PAGE followed by immunoblotting with anti-HA mAb showed that the chimeric protein and its degradation product both efficiently formed disulfide-linked dimers based on their reduced migration rates relative to the common non-specific band (FIG. 3C, lane 1).

Surface scFv Dimers are Active

Figure 4:
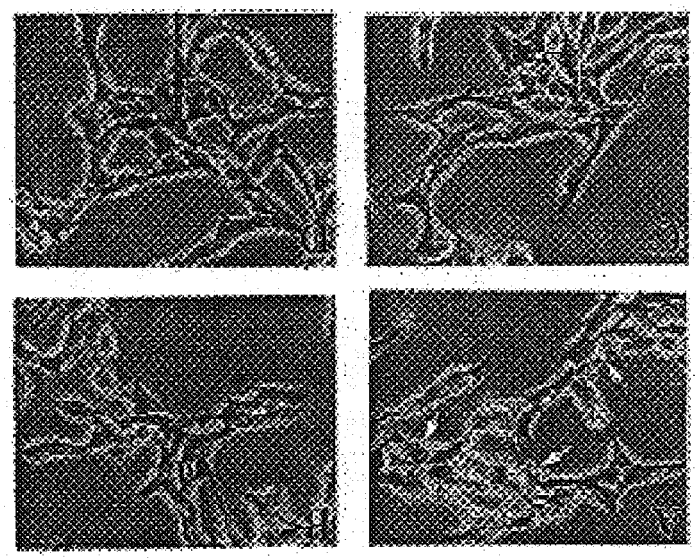
FIG. 4(A–D) is the T cells adhesion assay results showing T-cells bound to BHK cells transduced with 2C11 scFv.

BHK cells that were transfected with p2C11-γ1-B7 (FIG. 4A) but not pcDNA3 (FIG. 4C) were able to bind nylon-wool enriched lymphocytes, showing that 2C11-γ1-B7 was active. In this experiment, BHK cells transfected with p2C11-γ1-B7 (A and B) or pcDNA3 (C and D) were cultured overnight in 6-well plates before T-cells were added for 3 h at room temperature. 50 μg of mAb 145.2C11 was added to compete for CD3 epsilon on T-cells in B and D. Non-adherent cells were removed and the adherent cells were fixed and stained with methylene blue. T-cells bound to BHK/2C11 cells (A) are indicated with arrows. Over 95% of adherent lymphocytes positively stained for Thy-1.2 (results not shown), demonstrating that 2C11-γ1-B7 bound T cells. Binding of T cells to transfected BHK cells was mediated by specific interactions between 2C11-γ1-B7 on BHK cells and CD3 on lymphocytes because addition of free mAb 145.2C11 completely blocked binding (FIG. 4B). These results show that 2C11-γ1-B7 specifically binds to the CD3 epsilon chain on T-cells.

Figure 5:
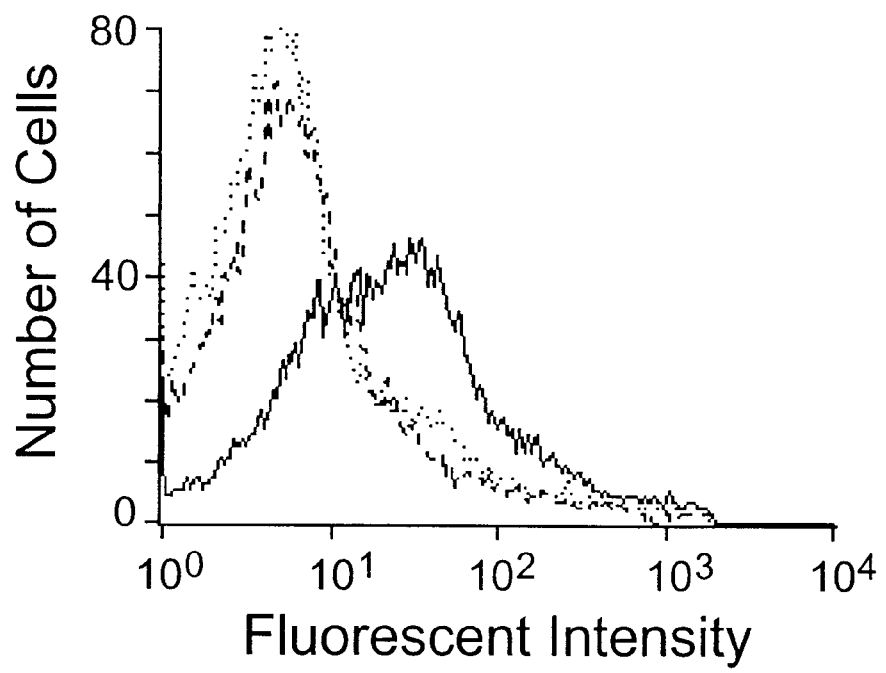
FIG. 5 is the immunofluorescence data showing the induction of IL-2 receptor α chain by 2C11 scFv.

The ability of 2C11-γ1-B7 anchored on the surface of BALB/3T3 cells to up-regulate CD25 (IL-2 receptor α-chain) expression on lymphocytes was examined by flow cytometry. BALB/3T3 cells ($10^5$) transfected with p2C11-γ1-B7 or pcDNA3 were cultured with $10^6$ splenocytes isolated from BALB/c mice for 2 days. Non-adherent cells were collected and analyzed for CD25 expression with rat anti-mouse CD25-FITC conjugate. The surface fluorescence of 10,000 naive splenocytes (dotted lined) or splenocytes cultured with BHK cells transfected with p2C11-γ1-B7 (solid line) or pcDNA3 (dashed line) was measured with a FACS caliber flow cytometer. FIG. 5 shows that culturing syngeneic splenocytes with BALB/3T3 cells previously transfected with p2C11-γ1-B7 resulted in increased surface expression of the IL-2 receptor compared with naive splenocytes or splenocytes that were cultured with BALB/3T3 cells transfected with pcDNA3.

Figure 6:
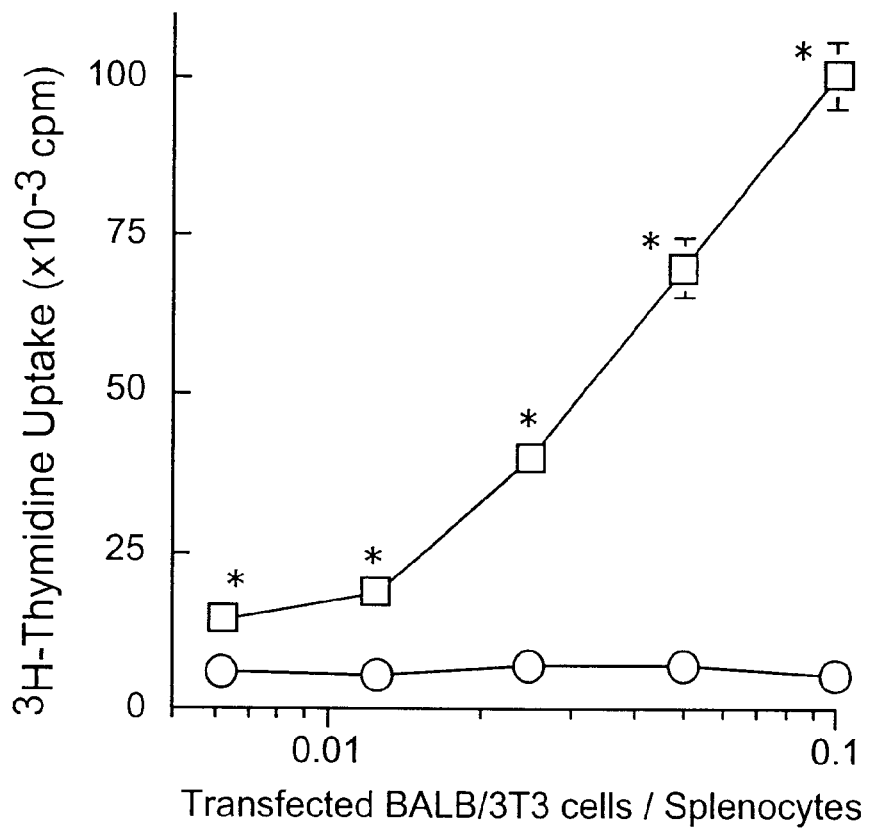
FIG. 6 shows splenocyte proliferation induced by 2C11 scFv.

2C11-γ1-B7 on BALB/3T3 cells also induced the proliferation of splenocytes. Serial dilutions of lethally irradiated BALB/3T3 cells transfected with pcDNA3 (open circles) or p2C11-γ1-B7 (open squares) were cultured with syngeneic splenocytes for 2 days. Cells were pulsed with 1 μCi [$^3$H]-thymidine for 16 h before the nonadherent cells were harvested and radioactivity was measured on a TopCount Microplate Scintillation Counter. Significant differences between $^3$H-thymidine incorporation of splenocytes cultured with 2C11-γ1-B7 or pcDNA3 transfected cells are indicated (*, $p \leq 0.0005$). Bars show the standard error of the mean. FIG. 6 shows that BALB/3T3 cells transfected with p2C11-γ1-B7 but not pcDNA3 stimulated $^3$H-thymidine incorporation of splenocytes in a dose-dependent fashion. Significant incorporation of $^3$H-thymidine was observed even when only 1 transfected BALB/3T3 cell was added per 160 splenocytes.

Induction of Cytotoxic Lymphocytes

Figure 7:
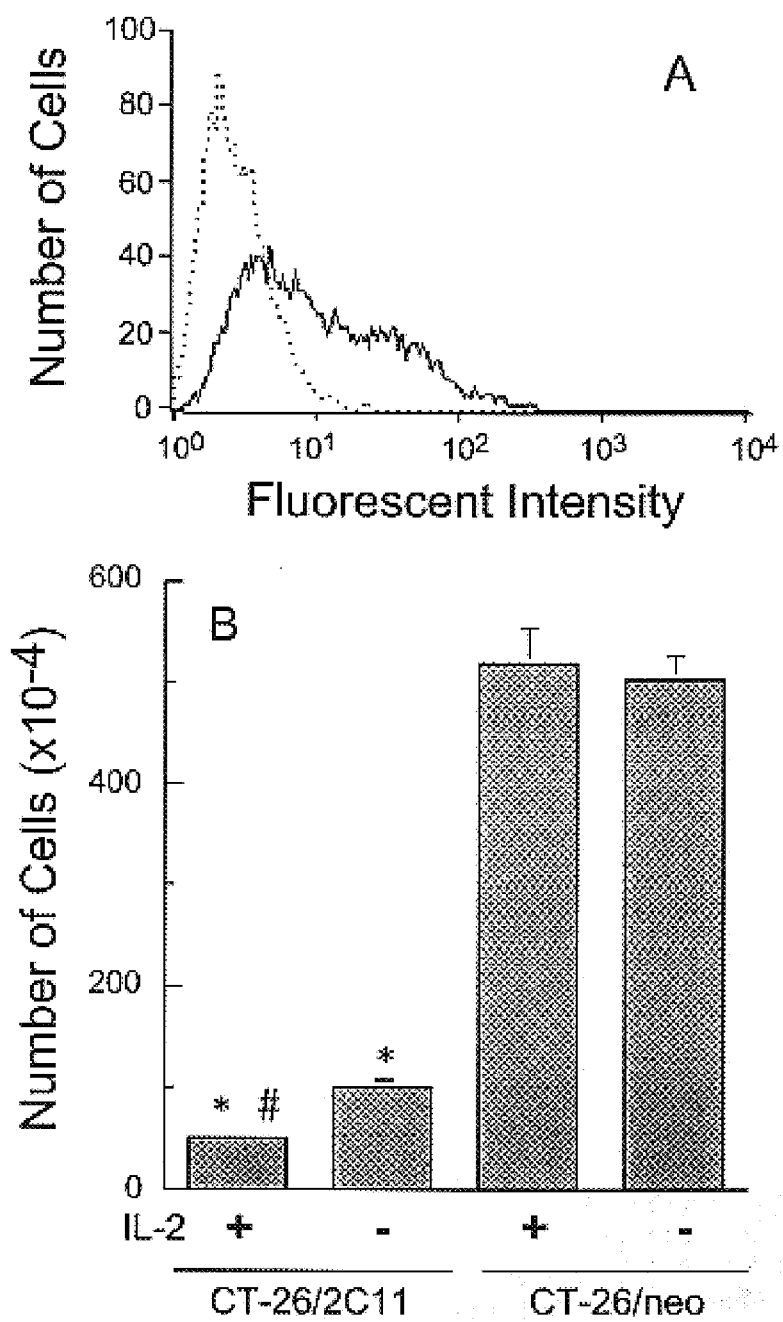
FIG. 7(A–B) shows the increase of splenocyte cytotoxic activity induced by 2C11 scFv.

CT26 colon carcinoma cells were infected with recombinant retrovirus to produce cell lines that expressed 2C11-γ1-B7 (CT26/2C11) or vector alone (CT26/neo). Flow cytometer analysis of the cells showed that about 41% of the CT26/2C11 cells expressed 2C11scFv dimers on their surface (FIG. 7A). In this experiment, CT26/2C11 (solid line) or CT26/neo (dashed line) cells were stained with mAb 12CA5 against the HA epitope and FITC-conjugated goat anti-mouse IgG (Fab')$_2$ before the immunofluorescence of $10^4$ viable cells was measured with a FACS caliber flow cytometer.

FIG. 7B shows that syngeneic splenocytes incubated with CT26/2C11 cells produced significant ($p \leq 0.05$) cytotoxicity against the CT26/2C11 cells compared to splenocytes incubated with CT26/neo cells. IL-2, although not required for cytotoxicity, did significantly ($p \leq 0.05$) enhance killing of CT26/2C11 cells. Activated splenocytes killed over 80% of CT26/2C11 cells even though only about 40% of the cell population expressed 2C11-γ1-B7 on their surface (FIG. 7A), suggesting that parental CT26 cells were also killed by activated splenocytes. In this experiment, CT26/2C11 or CT26/neo cells ($5 \times 10^5$) were cultured with or without 200 U/ml human IL-2 and $10^7$ naive syngeneic splenocytes for 2 days before adherent cells were harvested and counted under a light microscope. Significant differences between the mean number of CT26/2C11 and CT26/neo cells (*, $p \leq 0.005$) or between the mean number of CT26/2C11 cells with or without IL-2 (#, $p \leq 0.05$) are indicated. Bars show the standard error of the mean.

Figure 8:
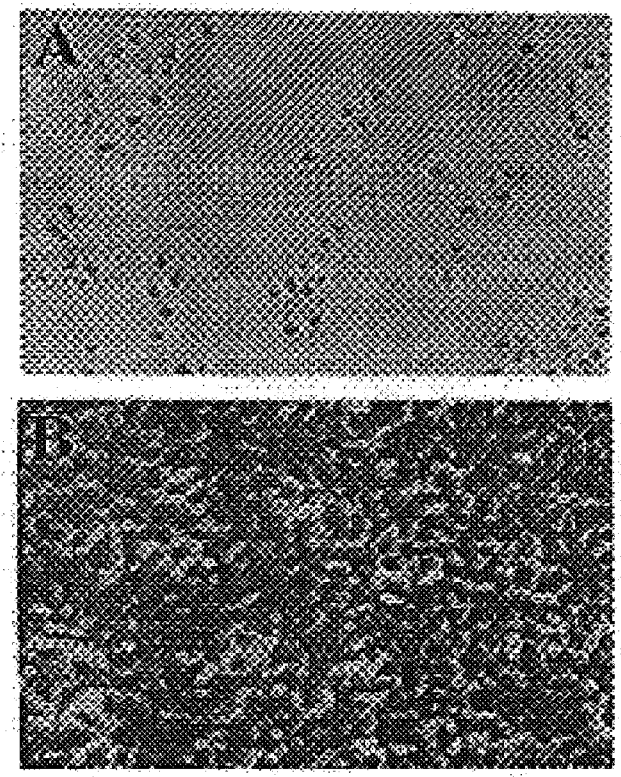
FIG. 8(A–B) shows cytotoxicity of the splenocytes activated by 2C11 scFv.

To test whether parental CT26 cells could be killed by activated splenocytes, naive syngeneic splenocytes ($5 \times 10^6$) were cultured with irradiated CT26/2C11 (A) or CT26/neo (B) cells in 200 U/ml human IL-2 for 2 days. The non-adherent cells ($10^7$) were collected and incubated with parental CT26 cells ($5 \times 10^5$ cells) in 20 U/ml human IL-2 for 48 h. Adherent cells were fixed, stained with methylene blue and photographed. Splenocytes that were pre-activated with the CT26/2C11 (FIG. 8A) but not CT26/neo cells (FIG. 8B) exhibited strong cytotoxicity to parental CT26 cells.

In vivo Activity

Figure 9:
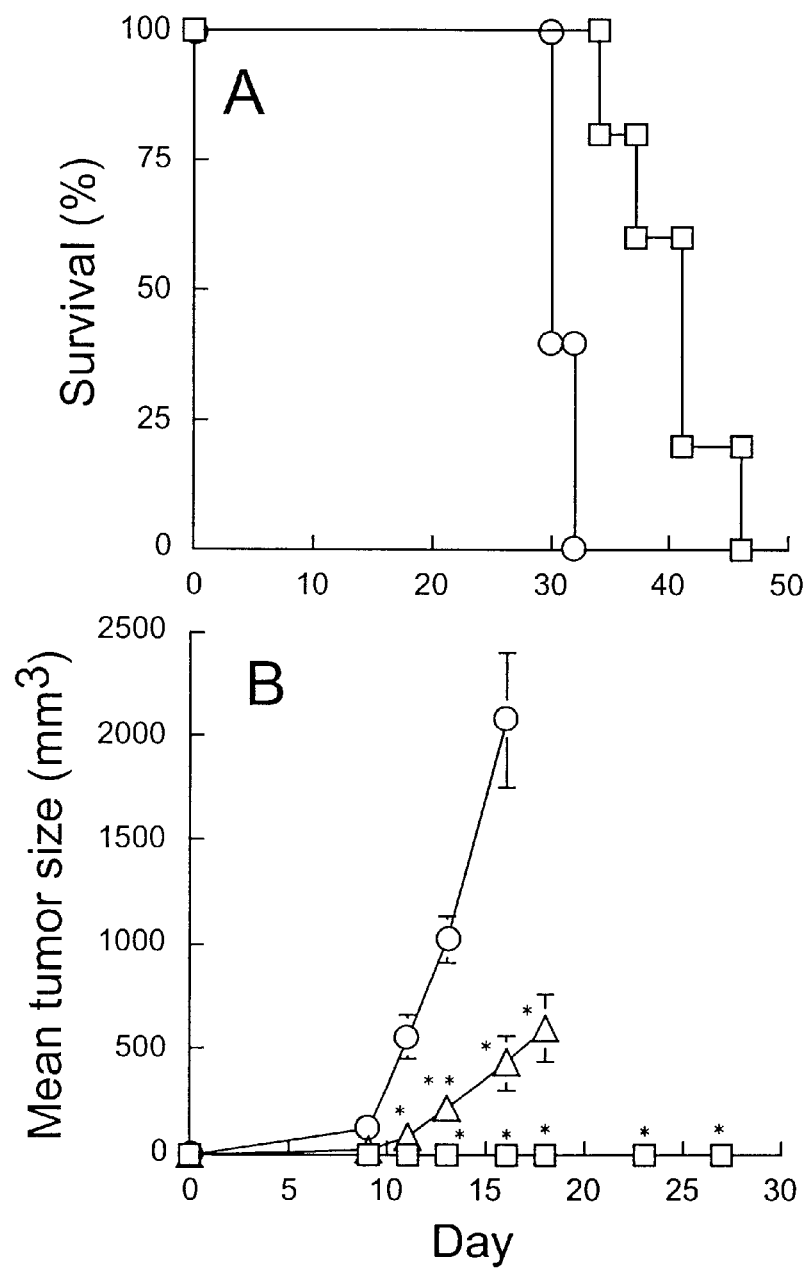
FIG. 9(A–B) shows in vivo effects of 2C11 scFv on tumor cells.

Immunization of BALB/c mice with radiation-killed CT26/2C11 cells 2 weeks before challenge with parental CT26 cells failed to induce protective immunity in BALB/c mice (FIG. 9A). In this experiment, groups of 5 BALB/c mice were untreated (O) or s.c. injected with $10^6$ radiation-killed CT26/2C11 cells ( ) 2 weeks before i.v. injection of $5 \times 10^4$ viable CT26 cells. In contrast, viable CT26/2C11 cells that were enriched for 2C11-γ1-B7 expression by cell sorting were completely rejected in BALB/c mice (FIG. 9B). In this experiment, groups of 6 BALB/c mice were s.c. injected with $5 \times 10^5$ viable CT26/neo (O) or CT26/2C11 ( ) cells or a mixture of $5 \times 10^5$ CT26/neo and $5 \times 10^5$ CT26/2C11 cells (Δ). Significant differences between the mean size of CT26/neo and other tumors are indicated: *, $p \leq 0.005$; **, $p \leq 0.0005$. Coinjection of equal numbers of CT26/2C11 and CT26/neo cells resulted in significant suppression of tumor growth compared to CT26/neo tumors in BALB/c mice, demonstrating in vivo bystander killing of tumor cells that did not express 2C11-γ1-B7. Flow cytometer analysis of tumor cells recovered from mixed tumors on day 18 failed to detect 2C11-γ1-B7, indicating that CT26/2C11 cells were eliminated from mixed tumors in vivo (results not shown).

Co-stimulation with CD80 or CD86 Enhance the Anti-tumor Effects of 2C11 scFv

T cells recognise peptides derived from tumor-associated antigens in association with MHC class I molecules on their surface. Full activation of T cells, however, requires costimulation in addition to signaling via the TCR. The most characterized costimulatory molecules are B7-1 (CD80) (McHugh et al. 1995) and B7-2 (CD86) (Freeman et al. 1993). These surface proteins interact with CD28 on T cells and deliver costimulatory signals to induce T-cell proliferation and IL-2 secretion (Lenschow et al. 1996). Tumor cells that have been engineered to express B7-1 or B7-2 are often rejected by CD8$^+$ T cells (Fujii et al. 1996; Hayakawa et al. 1997; Martin et al. 1999).

As previously mentioned, many tumors display defects in antigen processing and presentation that is a result of the loss or down regulation of proteosome subunits, TAP-1, TAP-2, β2-microglobulin or MHC class I heavy chain. Low numbers of MHC class I molecules or antigen on tumor cells may fail to activate T cells or prevent tumor cell recognition by cytotoxic T cells. Transduction of poorly immunogenic tumors with B7-1, thus, fails to induce tumor rejection (Chen et al. 1994; Habicht et al. 1995; Yang et al. 1995; Chong et al. 1996; Williams et al. 1996; Aruga et al. 1997; Chen 1997; Kerkmann Tucek et al. 1998). Anti-CD3 scFv dimers expressed on the surface of tumor cells are expected to provide the signal normally generated by the interaction of MHC-peptide complexes with the T cell receptor to activate T cells. In this way, costimulation provided by B7-1 or B7-2 may be effective even in tumors that are normally not rejected when transduced with these costimulatory molecules.

Figure 10:
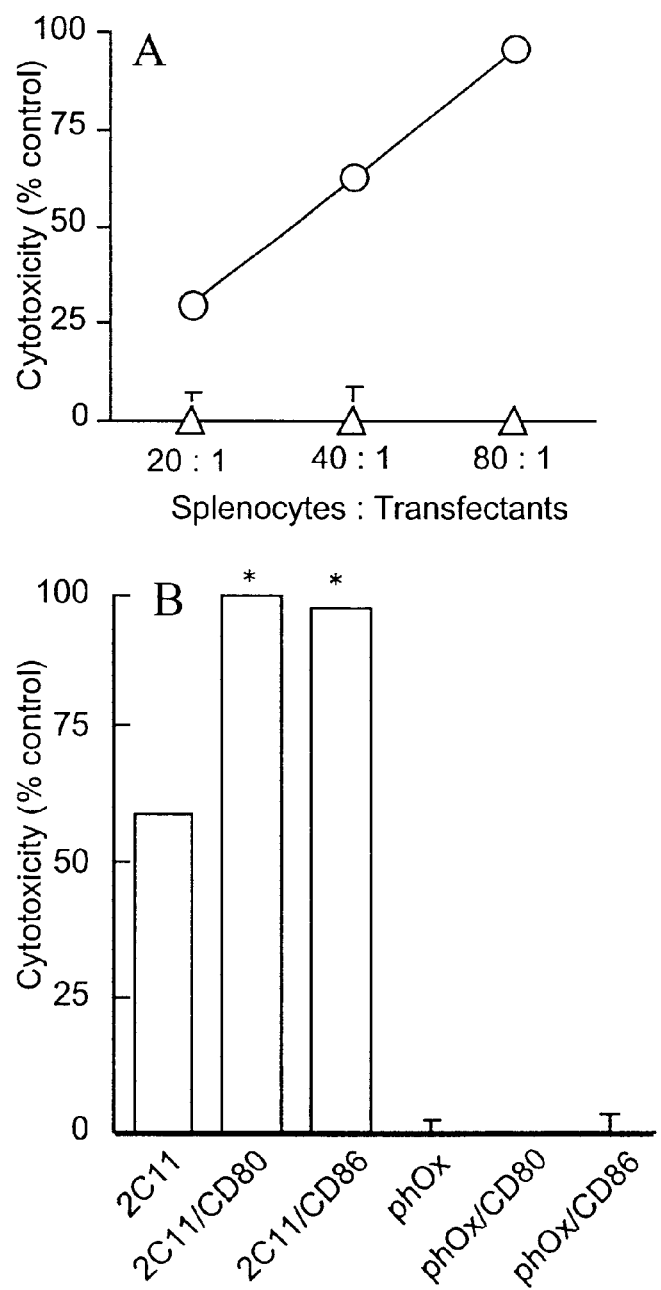
FIGS. 10(A–B) and 11 are test results showing the enhanced cytotoxicity of splenocytes or T lymphocytes when co-stimulated by C211 scFv with CD80 or CD86.

FIG. 10A shows that syngeneic splenocytes incubated with BALB/2C11 cells killed over 95% of transfectants after 72 h when 80 splenocytes were added per BALB/2C11 cell. In this experiment, different numbers of BALB/c splenocytes were cultured with 2.5×10$^5$ BALB/2C11 (O) or BALB/phOx ( ) cells in 6-well plates for 3 days. Viable attached cells were enumerated under a light microscope. Results represent mean values of 3 determinations. Significant differences between the cytotoxicity induced by BALB/2C11/CD80 or BALB/2C11/CD86 and 2C11 cells are indicated: *, p 0.0005. Bars show the standard error of the mean. Induction of lymphocyte cytotoxicity required expression of the 2C11 scFv on the surface of cells because BALB/phOx cells (cells expressing a control transgene which is similar to 2C11-γ1-B7 in construction but has 2C11 replaced with phOx) were not killed even at the highest ratio of splenocytes to transfectants. The effect of costimulation on lymphocyte cytotoxicity was investigated using a fixed ratio of 40 lymphocytes per transfectant. FIG. 10B shows that under these conditions, over 95% of BALB/2C11/CD80 and BALB/2C11/CD86 cells were killed compared to 58% of BALB/2C11 cells, demonstrating the enhancement provided by co-stimulation with CD80 (or CD86). In this example, 10$^7$ purified T lymphocytes were cultured for 3 day with 2.5×10$^5$ transfectants.

Figure 11:
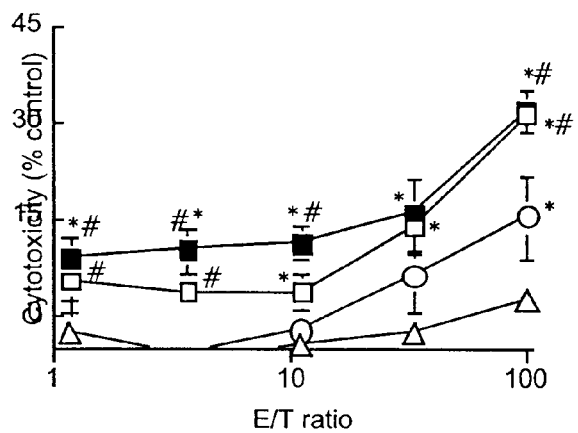

The cytotoxic activity of T cells that were activated by culture with different transfectants for 48 h before transfer to wells containing parental K-BALB cells was investigated. T cells were activated with mitomycin C-treated BALB/phOx ( ), BALB/2C11 (O), BALB/2C11/CD80 (□) or BALB/2C11/CD86 (■) cells for 48 h before lymphocytes were transfered to wells containing $^3$H-thymidine-labelled K-BALB (target) cells. The cells were harvested 5 h later and radioactivity was measured on a TopCount Microplate Scintillation Counter. Significant differences between the cytotoxicity induced by preactivation of lymphocytes with BALB/2C11, BALB/2C11/CD80 or BALB/2C11/CD86 cells compared with BALB/phOx cells are indicated: *, p 0.05. Significant differences between the cytotoxicity induced by preactivation of lymphocytes with BALB/2C11/CD80 or BALB/2C11/CD86 cells compared with BALB/2C11 cells are indicated: #, p 0.05. Bars indicate the standard error of the mean. FIG. 11 shows that splenocytes activated by BALB/2C11, BALB/2C11/CD80 and BALB/2C11/CD86 cells exhibited significantly greater cytotoxicity against K-BALB cells compared with phOx cells. Splenocytes activated by BALB/2C11/CD80 or BALB/2C11/CD86 cells produced significantly greater cytotoxicity than splenocytes cultured with BALB/2C11 cells ($p \leq 0.05$) at most E/T ratios.

Figure 12:
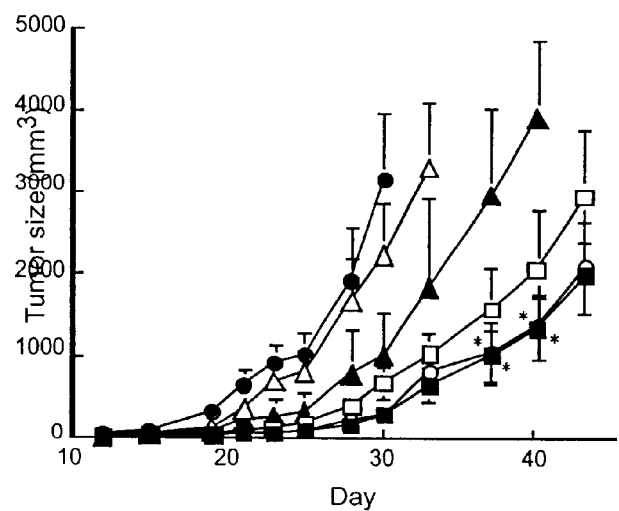
FIG. 12 shows the effects of the C211 scFv on tumors in vivo are enhanced by co-stimulator CD80 or CD86.

As shown in FIG. 12, the in vivo antitumor activity of 2C11 scFv was also enhanced by costimulation. Because BALB/3T3 cells are not tumorigenic, the in vivo cytotoxicity of BALB/2C11, BALB/2C11/CD80 and BALB/2C11/CD86 cells was examined by mixing these cells with K-BALB tumor cells. Groups of 6 female BALB/c mice were s.c. injected with 5×10$^5$ viable K-BALB tumor cells mixed with 1.5×10$^6$ BALB/3T3 (●), BALB/phOx ( ), BALB/phOx/CD86 (▲), BALB/2C11 (O), BALB/2C11/CD80 (□) or BALB/2C11/CD86 (■) cells. Significant differences between the mean tumor size of the BALB/phOx/CD86 group and the BALB/2C11 or BALB/2C11/CD86 groups are indicated: *, p 0.05. Bars represent the standard error of the mean. The growth rates of K-BALB tumors mixed with untransfected BALB/3T3 or BALB/phOx cells were similar, indicating that that human Fc region present in the chimeric scFv did not provide antitumor activity. BALB/phOx/CD86 cells, in which the control scFv was coexpressed with CD86, produced a modest delay in tumor growth compared to BALB/phOx cells alone, indicating that costimulation provided in trans allowed the generation of some antitumor activity. Coinnoculation of BALB/2C11/CD80 and BALB/2C11/CD86 cells with K-BALB tumor cells significantly inhibited tumor growth compared with BALB/phOx cells ($p \leq 0.005$). Surprisingly, BALB/2C11 cells were as effective as BALB/2C11/CD86 cells in inhibiting tumor growth although all mice treated with BALB/2C11 cells eventually formed tumors whereas one of six mice treated with BALB/2C11/CD80 or BALB/2C11/CD86 cells remained tumor free.

Figure 13:
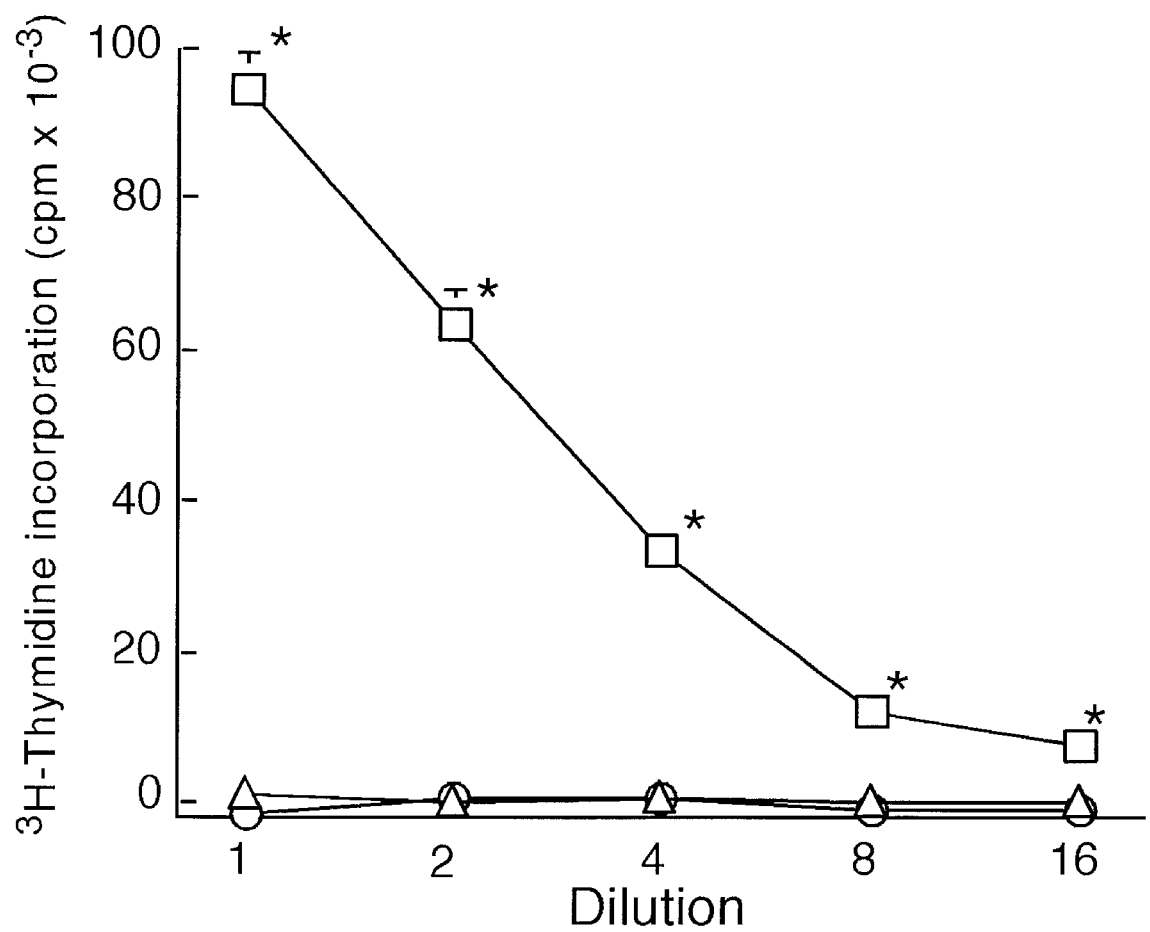
FIG. 13 shows that B16/F1 melanoma cells are rejected when 2C11 scFv and CD86 are both expressed on these cells.

Poorly immunogenic B16/F1 melanoma cells were also transduced with 2C11 scFv and B7 costimulation molecules. After drug selection, stable cell populations were isolated that expressed 2C11 scFv on their surface (F1/2C11 cells) as well as B16/F1 cells that expressed both 2C11 scFv and B7-1 (F1/2C11/CD80) or 2C11 scFv and B7-2 (F1/2C11/CD86). B16/F1 cells were also engineered to express a control phOx scFv (F1/phOx cells) as well as phOx scFv with B7-1 (F1/phOx/CD80) or phOx scFv with B7-2 (F1/phOx/CD86). C57/B16 mice were injected with equal numbers of B16/F1(□), F1/phOx (Δ), F1/2C11 (O), F1/2C11/CD80 (■), F1/2C11/CD86 (●), F1/phOx/CD80 (▲), or F1/phOx/CD86 (♦) cells on day 0. FIG. 13 shows that parental B16/F1 cells rapidly formed large tumors. Mice were killed on day 17 due to the large size of the tumors. Expression of control phOx scFv on B16/F1 cells did not provide anti-tumor activity as demonstrated by the rapid growth of F1/phOx cells. Expression of B7-1 or B7-2 on B16/F1 cells resulted in delayed tumor growth, but these poorly immunogenic cells still formed large tumors. Expression of 2C11 scFv alone or 2C11 scFv with B7-1 on B16/F1 cells produced strong anti-tumor activity but 75% of mice injected with F1/2C11 cells and 100% of mice injected with F1/2C11/CD80 cells had formed small tumors by day 25. In contrast, 100% of the mice injected with F1/2C11/CD86 cells (expressing both 2C11 scFv and B7-2 on B16/F1 cells) were tumor free on day 25. This result shows that expression of 2C11 scFv with CD86 can cause the rejection of a poorly immunogenic tumor in a syngenic host.

The γ1 Spacer Reduces Cleavage of 2C11 scFv Chimeric Proteins

Figure 14:
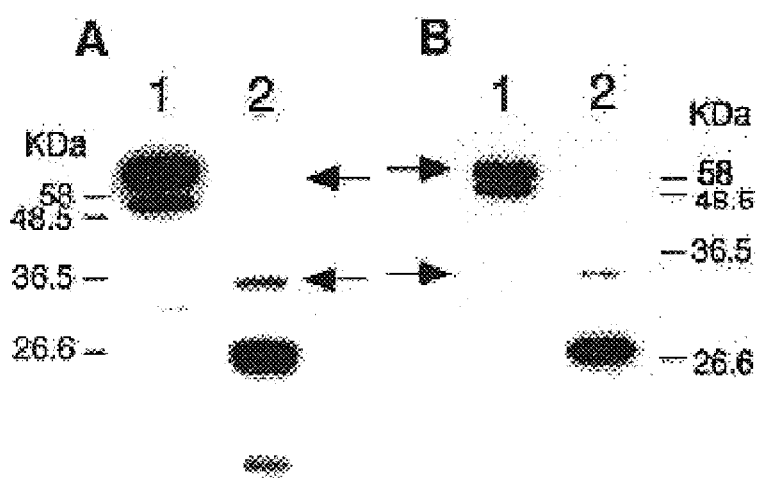
FIG. 14(A–B) is a western blot that shows the γ1 domain reduced degradation of scFv.

The cleavage of chimeric scFv proteins was examined by transfecting scFv transgenes into BHK cells and immunoblotting total cell lysates 48 h later (FIG. 14). In this example, p2C11-γ1-B7 (Lane 1) or p2C11-B7 (lane 2) were transfected into BHK cells. 48 h later, 5×10$^4$ cells were electrophoresed on an 8% reducing gel, transferred to nitrocellulose paper and probed with anti-HA antibody. (B). BHK cells were transfected with p2C11-γ1-B7 (Lane 1) or p2C11-B7 (lane 2) and 48 h later total cell lysates were electrophoresed on an 8% gel. After transfer to nitrocellular paper, blot was probed with anti-myc antibody. The positions of the undegraded chimeric scFv are indicated by arrows. FIG. 14A shows that only about 10% of 2C11-B7 (lane 2) possessed the expected molecular size of 34 kDa whereas 90% was present in a degraded form with a molecular size of 26 kDa. In contrast, about 60% of 2C11-γ1-B7 (lane 1) was present in the intact form (60 kDa) with 40% present as a degradated product (52 kDa). scFv chimeric proteins were cleaved at the C-terminal end because the degradation products retained the HA epitope present at the N-terminal of the chimeric proteins. To further localize the cleavage site, chimeric proteins containing a c-myc epitope between the scFv and PDGFR TM were immunoblotted with anti-myc antibody. FIG. 14B shows that similar to B7 chimeric proteins, about 90% of 2C11-PDGFR (lane 2) was degraded whereas 50% of 2C11-γ1-PDGFR (lane 1) was present in the intact form. The degradation products retained the myc epitope, indicating that the cleavage site was between the myc epitope and TM domain.

The γ1 Spacer can Maitain the Activity of Surface 2C11scFv Chimeric Proteins

Figure 15:
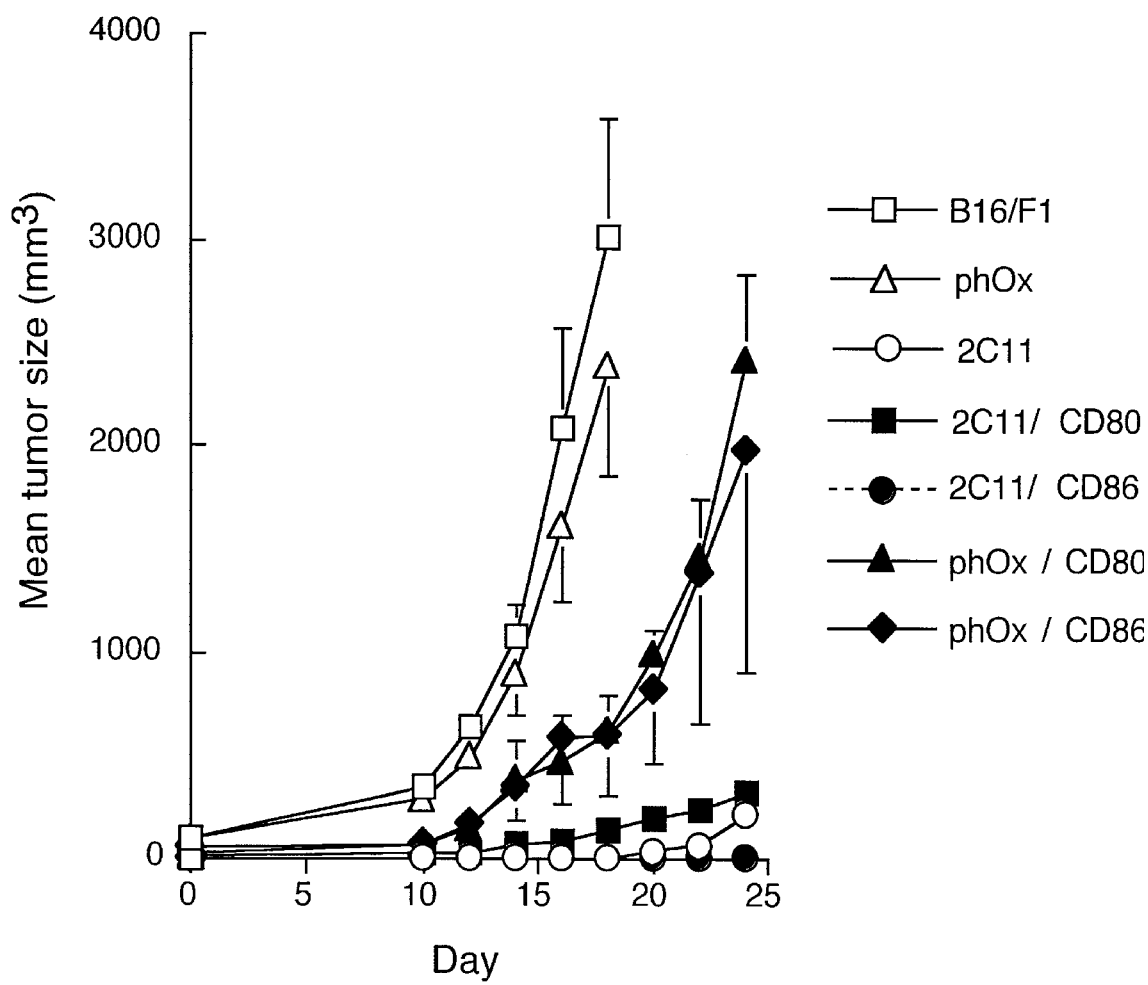
FIG. 15 shows that the γ1 spacer is required for scFv activation of splenoctes.

Serial dilutions of lethally-irradiated BALB/3T3 cells transfected with p2C11-γ1-B7 (□), p2C11-B7 ( ) or pcDNA3 (O) were cultured with syngeneic splenocytes for 2 days. Cells were pulsed with 1 $\mu$Ci [$^3$H]-thymidine for 16 h before the nonadherent cells were harvested and radioactivity was measured. Significant differences between splenocytes proliferation induced by BALB/3T3 cells transfected with p2C11-γ1-B7 or p2C11-B7 are indicated (*, p 0.0005). Bars show the standard error of the mean. BALB/3T3 cells transiently transfected with p2C11-γ1-B7 induced significant proliferation of naive splenocytes compared with pcDNA3 (FIG. 15). In contrast, 2C11-B7 did not induce significant T-cell proliferation compared with pcDNA3 even though 2C11-B7 fusion protein was expressed on the surface of transfected cells (results not shown). T cells bound to BALB/3T3 cells transfected with p2C11-γ1-B7 but not to cells tansfected with p2C11-B7, indicating that 2C11-B7 was unable to bind CD3 on T cells (results not shown).

The specific materials and methods employed in the foregoing embodiment are further described in the following.

Reagents mAb S5A8 against 38C13 lymphoma cells (Maloney et al. 1985) was kindly provided by Dr. Mi-Hua Tao, Academia Sinica, Taipei, Taiwan. mAb 12CA5 against an epitope of the hemagglutinin protein (HA) of human influenza virus was from Boehringer Mannheim Biochemical Co., Mannheim, Germany. Rat anti-mouse CD25-FITC conjugate was purchased from PharMingen, San Diego, Calif. Recombinant human IL-2 was from Cetus, USA. Cell lines and tissue culture BHK-21 cells were purchased from the American Type Culture Collection, Manassas, Va. BALB/3T3 cells were obtained from the NHRI Cell Bank (Taiwan), Bosc-23 cells (Pear et al. 1993) were kindly provided by Dr. Wen-Chang Lin, Academia Sinica, Taipei, Taiwan, and CT26 cells (Belnap et al. 1979) were kindly provided by Dr. Mi-Hua Tao, Academia Sinica, Taipei, Taiwan. 145.2C11 hybridoma cells were kindly provided by Dr. Jeffrey A. Bluestone, Ben May Institute for Cancer Research, Illinois, USA. Cells were cultured in Dulbecco's minimal essential medium (Sigma, St. Louis, Mo.) supplemented with 10% bovine serum, 100 units/ml penicillin and 100 mg/ml streptomycin at 37° C. in an atmosphere of 5% $CO_2$.

Plasmid Construction

The variable light ($V_L$) and heavy ($V_H$) chain cDNA sequences of mAB145.2C11 were amplified by RT-PCR from RNA isolated from 145.2C11 hybridoma cells as described (Chou et al. 1999). In the first round of PCR, primers P1 (5'-TGC TGG GGC CCA GCC GGC CGA CAT CCA GAT GAC CCA GTC TCC ATC-3') (SEQ ID NO: 1) and P2 (5'-ACC GCC GCC CGA AGT ACT GCC CCG TTT GAT TTC CAG CTT GGT GCC AGG-3') (SEQ ID NO: 2) were employed to introduce a Sfi I restriction enzyme site at the 5'-end (bold) and half of the linker (underlined) at the 3' end of the $V_L$ cDNA, respectively. Similarly, primers P3 (5'-AAG TCG AGT GAG GGT AAG GGT GAG GTG CAG CTG GTG GAG TCT GGG GGA-3') (SEQ ID NO: 3) and P4 (5'-TGT TGT GTC GAC TGA GGA GAC GGT GAC CAT GGT TCC TTG-3') (SEQ ID NO: 4 were employed to introduce the other half of the linker (underlined) to the 5' end and a Sal I restriction site (bold) at the 3' end of the amplified $V_H$ cDNA. The $V_L$ and $V_H$ PCR products were assembled in a second round of PCR with primers P1, P4 and a linker primer P5 (5'-GGC AGT ACT TCG GGC GCC GGT AAG TCG AGT GAG GGT MG GGT-3') (SEQ ID NO: 5) encoding a 14 amino acid residue linker peptide GSTSGAGKSSEGKG (SEQ ID NO: 6) (Solar and Gershoni 1995). The PCR product was digested with Sfi I and Sal I restriction enzymes and subcloned into pHook-1 (Invitrogen, Leek, The Netherlands) in place of the phOx scFv cDNA to obtain p2C11-PDGFR. The Sal I-Xho I fragment encoding a myc epitope and the PDGFR TM in p2C11-PDGFR was replaced with a Sal I-Xho I fragment from pAFP-B7 (Chou et al. 1999) encoding the murine B7-1 TM and cytosolic tail (Pro237 to the stop codon) to create p2C11-B7. A Sal I fragment containing the hinge, $CH_2$ and $CH_3$ domain (γ1) of the human $IgG_1$ heavy chain from pAFP-γ1-B7 (Chou et al. 1999) was inserted into the unique Sal I site in p2C11-PDGFR and p2C11-B7 to produce p2C11-γ1-PDGFR and p2C11-γ1-B7. All transgenes were fully sequenced.

Transfection of Transgenes $2.5 \times 10^5$ BHK or BALB/3T3 cells per well were cultured overnight in 6-well plates before transfection with 3 $\mu$g plasmid and 10 $\mu$l lipofectamine according to the manufacturer's instructions (Gibco Laboratories, Grand Island, N.Y.). BHK or BALB/3T3 cells transfected with pcDNA3 or p2C11-γ1-B7 were also selected in 0.5 mg/ml G418 (Calbiochem, San Diego, Calif.) for 2 weeks to produce the stable transfectant clones BHK/neo, BHK/2C11, BALB/neo and BALB/2C11, respectively.

BALB/3T3 and B16/F1 cells cells were also transfected with p2C11-γ1-B7 or pOx-γ1-B7 and selected in 0.5 mg/mL G418 (Calbiochem, San Diego, Calif.). These cells were sorted for high expression to produce stable 2C11 and phOx cells. The scFv transgenes were also cotransfected into BALB/3T3 and B16/F1 cells with pB7-1/zeo or pB7-2/zeo. The transfected cells were selected in 0.5 mg/mL G418 and 0.5 mg/mL zeocin (Invitrogen) for 2 weeks before they were sorted for high expression to produce the stable transfectants 2C11/CD80, 2C11/CD86, phOx/CD80 and phOx/CD86 based on a BALB/3T3 or B16/F1 background as indicated in the text.

A. Flow Cytometer Analysis $5 \times 10^5$ cells were washed and suspended in DMEM containing 0.5% bovine serum and 5 $\mu$g/ml mAb 12CA5 (anti-HA) or mAb S5A8 (control) for 60 min at 4° C. Cells were washed and incubated with FITC-conjugated goat anti-mouse IgG (Fab')$_2$ (1:200, Organon Teknika, Durham, N.C.) for 60 min. Cells were also stained with goat anti-human IgG Fc-FITC conjugate (1:1000, Organon Teknika) to detect the presence of the γ1 domain. 2C11/CD80 and phOx/CD80 cells were also stained with rat anti mouse CD80-biotin conjugate (1:500) and FITC-conjugated streptavidin (1:200). 2C11/CD86 and phOx/CD86 cells were stained with rat anti-mouse CD86 biotin-conjugate (1:500) and FITC-conjugated streptavidin (1:200). Cells were washed and suspended in PBS containing 5 $\mu$g/ml propidium iodide before the surface immunofluorescence of $10^4$ viable cells was measured with a FACScaliber flow cytometer (Becton Dickinson, Mountain View, Calif.). Dead cells, identified by red propidium iodide fluorescence, were gated out. Fluorescence intensities were analyzed with Cell Quest Software (Becton Dickinson).

Immunoblotting of Chimeric Proteins $5 \times 10^4$ BHK/neo or BHK/2C11 cells were boiled in SDS-PAGE buffer with or without 2-mercaptoethanol. Proteins were electrophoresed on an 8% SDS-PAGE and transferred to two sheets of nitrocellulose paper (Gelman Sciences, Ann Arbor, Mich.) in transfer buffer (10 mM Tris-HCl, pH 7.5, 50 mM NaCl, 2 mM EDTA, 0.5 mM 2-mercaptoethanol) by capillary diffusion. Blots were blocked with 5% skim milk and incubated with 5 $\mu$g/ml mAb 12CA5 or HRP-conjugated goat anti-human Fc-specific (1:1000, Sigma) in 0.1% Tween-20/PBS for 60 min. Blots were extensively washed in the same buffer, incubated with HRP-conjugated goat anti-mouse IgG (Fab')$_2$ (1:2000) for 60 min, washed, and developed. Under reducing condition, blots were visualized by ECL detection according to the manufacturer's instructions (Pierce, Rockford, Ill.). Under non-reducing conditions, blots were visualized with 4-chloro-1-naphthol (Sigma Chemical Co., St. Louis, Mo.) substrate.

T-cell Adhesion Assay $2 \times 10^5$ BHK/neo or BHK/2C11 cells/well were cultured overnight in 6-well plates. Splenocytes were isolated from BALB/c mice and cultured in RPMI 1640 medium (Sigma, St. Louis, Mo.) supplemented with 10% FCS and 20 U/ml human IL-2 overnight. $2 \times 10^7$ nylon wool-enriched lymphocytes were added to each well for 3 h at room temperature with or without 50 µg mAb 145.2C11. Non-adherent cells were removed by gently washing the wells 5 times with medium. Adherent cells were fixed and stained with methylene blue in 50% methanol and examined under a light microscope. Adherent lymphocytes were identified by first staining nylon wool-enriched lymphocytes with FITC-conjugated rat anti-mouse Thy-1.2 mAb (PharMingen, San Diego, Calif.) before addition to BALB/2C11 cells. Adherent lymphocytes were observed under both fluorescent and light illumination to estimate the fraction of bound T cells. IL-2 receptor chain (CD25) induction BALB/3T3 cells were transfected with p2C11-γ1-B7 or pcDNA3 48 h before $10^5$ cells were cultured with $10^6$ splenocytes isolated from BALB/c mice in 6-well plates for 2 days. Non-adherent cells were collected and incubated with FITC-conjugated rat anti-mouse CD25 (1:500) for 1 h at 4° C. The surface fluorescence of 10,000 viable cells was measured with a FACS caliber flow cytometer.

B. Splenocyte Proliferation

BALB/3T3 cells were transfected with pcDNA3 or p2C11-γ1-B7 48 h before they were lethally irradiated and serially diluted into round-bottom 96-well plates. To determine the activity of 2C11-B7 and 2C11-γ1-B7, BALB/3T3 cells were transfected with pchDNA3, p2C11-B7 or p2C11-γ1-B7 48 h before they were lethally irradiated and serially diluted into round-bottom 96-well plates. Splenocytes from BALB/c mice ($5 \times 10^5$ cells/well in RPMI 1640 supplemented with 10% FBS and 10 mM HEPES) were added to wells for 2 days. 1 µCi [$^3$H]-thymidine was added to wells for 16 h, cells were harvested, and the radioactivity was measured on a TopCount Microplate Scintillation Counter (Packard, Meriden, Conn.).

Generation of CT26 Tumor Cell Line Transfectants

The EcoR I fragment encoding the 2C11-γ1-B7 transgene was excised from p2C11-γ1-B7 and subcloned into the retroviral vector pBabe-neo (a kind gift from Dr. Hartmut Land, Imperial Cancer Research Fund, London, United Kingdom) to generate pBabe-2C11-γ1-B7. $10^6$ Bosc 23 packaging cells were transfected with 3 µg pBabe-2C11-γ1-B7 or pBabe-neo in 10 µl lipofectamine. After 48 h, 3 ml culture supernatant was incubated with $2 \times 10^5$ CT26 cells in 6-well plates for 48 h before adding 0.5 mg/ml G418 for 2 weeks to obtain CT26/neo and CT26/2C11 cells.

Induction of Splenocyte Cytotoxicity $5 \times 10^5$ CT26/2C11 or CT26/neo cells and $10^7$ BALB/c splenocytes were cultured with or without 200 U/ml human IL-2 in 6-well plates for 2 days. Non-adherent cells were removed and the wells were gently washed with PBS. Adherent cells were harvested with trypsin, stained with Trypan Blue and counted under a light microscope.

$2.5 \times 10^5$ 2C11 or phOx cells (tranduced BALB/3T3 cells) were incubated with $5 \times 10^6$, $1 \times 10^7$ or $2 \times 10^7$ splenocytes in 6-well plates for 3 days. Non-adherent cells were removed and the wells were gently washed with medium. Adherent cells were harvested with trypsin, stained with Trypan Blue and counted under a light microscope. $2.5 \times 10^5$ 2C11, 2C11/CD80, 2C11/CD86 or phOx cells were also incubated with $10^7$ T lymphocytes for 3 days and assayed for viability as above. Cytotoxicity was calculated as the number of viable transfectants remaining after incubation with immune cells divided by the number of viable transfectants in control wells that did not contain immune cells.

Cytotoxicity of Activated Splenocytes to Parental CT26 Cells $5 \times 10^5$ lethally-irradiated CT26/2C11 or CT26/neo cells and $5 \times 10^6$ BALB/c splenocytes were cultured with 200 U/ml IL-2 in 6-well plates for 2 days. Non-adherent cells (activated splenocytes) were harvested and counted. Parental CT26 cells were plated in 6-well plates at $5 \times 10^5$ cells/well with 20 U/ml human IL-2 and $10^7$ activated splenocytes. After 48 h, the non-adherent cells were removed by washing with PBS. Adherent cells were fixed and stained with 0.5% methylene blue in 50% methanol and examined under a light microscope.

JAM Assay $3.5 \times 10^7$ T cells were mixed with $3.5 \times 10^7$ mitomycin C-treated BALB/3T3 transfectants, centrifuged at 1500 rpm for 5 min and cultured for 72 h in 6 well plates. The activated T cells were harvested and mixed with K-BALB cells that had been labeled for 16 h in medium containing 50 µCi $^3$H-thymidine. Each U-botton well contained $10^4$ labeled K-BALB cells and the indicated number of activated T cells. The plate was centrifuged at 500 rpm for 2 min and incubated in a $CO_2$ incubator for 5 h at 37° C. The cells were harvested and the radioactivity was measured on a TopCount Microplate Scintillation Counter. The cytotoxic activity was calculated as Cytotoxicity%=[1−(total cpm-sample cpm)/total cpm]×100; where the total cpm was measured in wells in which T cells were not added to K-BALB cells.

C. In vivo Tumor Challenge

Groups of 5 female BALB/c were untreated or s.c injected with $10^6$ lethally-irradiated CT26/2C11 cells 2 weeks before mice were i.v. injected with $5 \times 10^4$ viable CT26 cells. Mice survival was monitored for 50 days.

In vivo Tumor Growth

Groups of 6 female BALB/c mice were s.c. injected with $5 \times 10^5$ viable CT26/neo or CT26/2C11 cells or a mixture of $5 \times 10^5$ CT26/neo and $5 \times 10^5$ CT26/2C11 cells. Tumor dimensions were measured with calipers and tumor volume was estimated as 0.5×height×width×length. Mice were killed when tumors reached 2000 mm$^3$. Some tumors were sterially removed, dissociated with 0.5 mg/ml collagenase, cultured in G418-containing medium for 3 days and then analyzed for 2C11-γ1-B7 expression by flow cytometry with FITC-conjugated goat anti-human IgG Fc-specific antibody as described above.

In a separate experiment, groups of 6 female BALB/c mice were s.c. injected with $5 \times 10^5$ viable K-BALB tumor cells mixed with $1.5 \times 10^6$ BALB/3T3 cells or transfectant cells. Tumor dimensions were measured with calipers and tumor volume was estimated as 0.5×height×width×length. Mice were killed when tumors reached 4000 mm$^3$.

Groups of four male C57/BL6 mice were also s.c. injected with $2 \times 10^6$ live B16/F1 cells or B16/F1 cells that stably expressed the following molecules on their surface: 2C11 scFv (2C11), 2C11 scFv and B7-1 (2C11/CD80), 2C11 scFv and B7-2 (2C11/CD86), phOx scFv (phOx), phOx scFv and B7-1 (phOx/CD80) or phOx scFv and B7-2 (phOx/CD86). Mice were killed when tumpor size exceeded 2.5 cm$^3$.

Statistical Analysis

Statistical significance of differences between mean values was estimated with the shareware program Schoolstat (White Ant Occasional Publishing, West Melbourne, Australia) using the independent t-test for unequal variances.

It is to be understood that the invention is not limited to the specific materials and methods described in the foregoing. Similar materials from different sources or equivalent assay equipment may be satisfactorily used. Further, although the embodiment described above was achieved in murines, it is contemplated that, by making certain adjustments known to people skilled in the art, the invention is applicable to other mammalian species, including humans. For example, a human version of 2C11-γ1-B7 can be made from anti-human CD3 and human B7-1 or B7-2.

References

Altenschmidt U, Klundt E and Groner B (1997) Adoptive transfer of in vitro-targeted, activated T lymphocytes results in total tumor regression. *J Immunol* 159: 5509–15.

Altenschmidt U, Moritz D and Groner B (1997) Specific cytotoxic T lymphocytes in gene therapy. *J Mol Med* 75: 259–66.

Alvarez Vallina L, Agha Mohammadi S, Hawkins R E and Russell S J (1997) Pharmacological control of antigen responsiveness in genetically modified T lymphocytes. *J Immunol* 159: 5889–95.

Aruga E, Aruga A, Arca M J, Lee W M, Yang N S, Smith J W, 2nd and Chang A E (1997) Immune responsiveness to a murine mammary carcinoma modified to express B7-1, interleukin-12, or GM-CSF. *Cancer-Gene-Ther* 4: 157–66.

Belnap L P, Cleveland P H, Colmerauer M E, Barone R M and Pilch Y H (1979) Immunogenicity of chemically induced murine colon cancers. *Cancer Res* 39: 1174–9.

Blades R A, Keating P J, McWilliam L J, George N J and Stern P L (1995) Loss of HLA class I expression in prostate cancer: implications for immunotherapy. *Urology* 46: 681–6.

Bolhuis R L, Sturm E and Braakman E (1991) T cell targeting in cancer therapy. *Cancer Immunol Immunother* 34: 1–8.

Chen L (1997) Manipulation of T cell response to tumors by targeting on costimulatory pathway. *Leukemia* 3: 567–9.

Chen L, McGowan P, Ashe S, Johnston J, Li Y, Hellstrom I and Hellstrom K E (1994) Tumor immunogenicity determines the effect of B7 costimulation on T cell-mediated tumor immunity. *J-Exp-Med* 179: 523–32.

Chong H, Hutchinson G, Hart J R and Vile R G (1996) Expression of co-stimulatory molecules by tumor cells decreases tumorigenicity but may also reduce systemic antitumor immunity. *Hum-Gene-Ther* 7: 1771–9.

Chou W C, Liao K W, Lo Y C, Jiang S Y, Yeh M Y and Roffler S R (1999) Expression of chimeric monomer and dimer proteins on the plasma membrane of mammalian cells. *Biotechnology and Bioengineering* 65: 160–169.

Freeman G J, Borriello F, Hodes R J, Reiser H, Gribben J G, Ng J W, Kim J, Goldberg J M, Hathcock K, Laszlo G, Lombard L A, Wang S, Gray G S, Nadler L M and Sharpe A H (1993) Murine B7-2, an alternative CTLA4 counter-receptor that costimulates T cell proliferation and interleukin 2 production. *J Exp Med* 178: 2185–92.

Fujii H, Inobe M, Kimura F, Murata J, Murakami M, Onishi Y, Azuma I, Uede T and Saiki I (1996) Vaccination of tumor cells transfected with the B7-1 (CD80) gene induces the anti-metastatic effect and tumor immunity in mice. *Int J Cancer* 66: 219–24.

Goldberg A L and Rock K L (1992) Proteolysis, proteasomes and antigen presentation. *Nature* 357: 375–9.

Habicht A, Lindauer M, Gaimbacher P, Rudy W, Gebert J, Schackert H K, Meuer S C and Moebius U (1995) Development of immunogenic colorectal cancer cell lines for vaccination: expression of CD80 (B7.1) is not sufficient to restore impaired primary T cell activation in vitro. *Eur-J-Cancer* 31a: 2396–402.

Hayakawa M, Kawaguchi S, Ishii S, Murakami M and Uede T (1997) B7-1-transfected tumor vaccine counteracts chemotherapy-induced immunosuppression and prolongs the survival of rats bearing highly metastatic osteosarcoma cells. *Int J Cancer* 71: 1091–102.

Kaklamanis L, Townsend A, Doussis Anagnostopoulou I A, Mortensen N, Harris A L and Gatter K C (1994) Loss of major histocompatibility complex-encoded transporter associated with antigen presentation (TAP) in colorectal cancer. *Am J Pathol* 145: 505–9.

Kerkmann Tucek A, Banat G A, Cochlovius B and Zoller M (1998) Antigen loss variants of a murine renal cell carcinoma: implications for tumor vaccination. *Int-J-Cancer* 77: 114–22.

Korkolopoulou P, Kaklamanis L, Pezzella F, Harris A L and Gatter K C (1996) Loss of antigen-presenting molecules (MHC class I and TAP-1) in lung cancer. *Br J Cancer* 73: 148–53.

Lenschow D J, Walunas T L and Bluestone J A (1996) CD28/B7 system of T cell costimulation. *Annu Rev Immunol* 14: 233–58.

Luboldt H J, Kubens B S, Rubben H and Grosse Wilde H (1996) Selective loss of human leukocyte antigen class I allele expression in advanced renal cell carcinoma. *Cancer Res* 56: 826–30.

Maeurer M J, Gollin S M, Storkus W J, Swaney W, Karbach J, Martin D, Castelli C, Salter R, Knuth A and Lotze M T (1996) Tumor escape from immune recognition: loss of HLA-A2 melanoma cell surface expression is associated with a complex rearrangement of the short arm of chromosome 6. *Clin Cancer Res* 2: 641–52.

Maloney D G, Kaminski M S, Burowski D, Haimovich J and Levy R (1985) Monoclonal anti-idiotype antibodies against the murine B cell lymphoma 38C13: characterization and use as probes for the biology of the tumor in vivo and in vitro. *Hybridoma* 4: 191–209.

Martin B K, Frelinger J G and Ting J P (1999) Combination gene therapy with CD86 and the MHC class II transactivator in the control of lung tumor growth. *J Immunol* 162: 6663–70.

McHugh R S, Ahmed S N, Wang Y C, Sell K W and Selvaraj P (1995) Construction, purification, and functional incorporation on tumor cells of glycolipid-anchored human B7-1 (CD80). *Proc Natl Acad Sci USA* 92: 8059–63.

Moritz D, Wels W, Mattern J and Groner B (1994) Cytotoxic T lymphocytes with a grafted recognition specificity for ERBB2-expressing tumor cells. *Proc Natl Acad Sci USA* 91: 4318–22.

Nouri A M, Hussain R F and Oliver R T (1994) The frequency of major histocompatibility complex antigen abnormalities in urological tumours and their correction by gene transfection or cytokine stimulation. *Cancer Gene Ther* 1: 119–23.

Pear W S, Nolan G P, Scott M L and Baltimore D (1993) Production of high-titer helper-free retroviruses by transient transfection. *Proc Natl Acad Sci USA* 90: 8392–6.

Restifo N P, Marincola F M, Kawakami Y, Taubenberger J, Yannelli J R and Rosenberg S A (1996) Loss of functional beta 2-microglobulin in metastatic melanomas from five patients receiving immunotherapy. *J Natl Cancer Inst* 88: 100–8.

Solar I and Gershoni J M (1995) Linker modification introduces useful molecular instability in a single chain antibody. *Protein Eng* 8: 717–23.

Tibben J G, Boerman O C, Massuger L F, Schijf C P, Claessens R A and Corstens F H (1996) Pharmacokinetics, biodistribution and biological effects of intravenously administered bispecific monoclonal antibody OC/TR F(ab')2 in ovarian carcinoma patients. *Int J Cancer* 66: 477–83.

Vitale M, Rezzani R, Rodella L, Zauli G, Grigolato P, Cadei M, Hicklin D J and Ferrone S (1998) HLA class I antigen and transporter associated with antigen processing (TAP1 and TAP2) down-regulation in high-grade primary breast carcinoma lesions. *Cancer Res* 58: 737–42.

Weiner L M, Clark J I, Ring D B and Alpaugh R K (1995) Clinical development of 2B1, a bispecific murine monoclonal antibody targeting c-erbB-2 and Fc gamma RIII. *J Hematother* 4: 453–6.

Williams I R, Ort R J, Daley D, Manning L, Karaoli T, Barnhill R L and Kupper T S (1996) Constitutive expression of B7-1 (CD80) on mouse keratinocytes does not prevent development of chemically induced skin papillomas and carcinomas. *J-Immunol* 156: 3382–8.

Yang G, Hellstrom K E, Hellstrom I and Chen L (1995) Antitumor immunity elicited by tumor cells transfected with B7-2, a second ligand for CD28/CTLA-4 costimulatory molecules. *J-Immunol* 154: 2794–800.

All references cited herein are incorporated by reference.

We claim:

1. A chimeric protein, comprising:
   a) a single chain antibody against CD3;
   b) a cytoplasmic domain comprising the B7-1 antigen; and
   c) the γ1 domain of human IgG$_1$ located between said single chain antibody and said cytoplasmic domain.

2. The chimeric protein of claim 1, wherein said single chain antibody is 2C11 scFv.

3. A mammalian tumor cell, comprising the chimeric protein in claim 1.

4. The mammalian tumor cell of claim 3, wherein said single chain antibody of said chimeric protein is 2C11 scFv.

* * * * *